(12) United States Patent
Djurling et al.

(10) Patent No.: US 8,452,416 B2
(45) Date of Patent: May 28, 2013

(54) MEDICAL LEAD ASSEMBLY AND METHOD FOR IMPLANTATION THEREOF

(75) Inventors: Henrik Djurling, Järfälla (SE); Rolf Hill, Järfälla (SE); Olof Stegfeldt, Älta (SE); Åsa Broomé, Järfälla (SE); Hans Strandberg, Sundbyberg (SE)

(73) Assignee: St. Jude Medical AB, Jarfalla (SE)

( * ) Notice: Subject to any disclaimer, the term of this patent is extended or adjusted under 35 U.S.C. 154(b) by 193 days.

(21) Appl. No.: 13/000,075

(22) PCT Filed: Jun. 27, 2008

(86) PCT No.: PCT/SE2008/000416
§ 371 (c)(1),
(2), (4) Date: Dec. 20, 2010

(87) PCT Pub. No.: WO2009/157818
PCT Pub. Date: Dec. 30, 2009

(65) Prior Publication Data
US 2011/0093053 A1   Apr. 21, 2011

(51) Int. Cl.
*A61N 1/05* (2006.01)
(52) U.S. Cl.
CPC .......................................... *A61N 1/05* (2013.01)
USPC ......................................................... 607/116

(58) Field of Classification Search
USPC ........................... 607/115–138; 600/372–381
See application file for complete search history.

(56) References Cited

U.S. PATENT DOCUMENTS

| | | | |
|---|---|---|---|
| 5,318,041 A | 6/1994 | DuBois et al. | |
| 5,833,604 A | 11/1998 | Houser et al. | |
| 6,249,708 B1 | 6/2001 | Nelson et al. | |
| 6,549,812 B1* | 4/2003 | Smits | 607/122 |
| 6,656,221 B2 | 12/2003 | Taylor et al. | |
| 6,728,579 B1 | 4/2004 | Lindgren et al. | |
| 8,010,207 B2 | 8/2011 | Smits et al. | |
| 2002/0077590 A1 | 6/2002 | Ponzi et al. | |
| 2002/0183824 A1 | 12/2002 | Borgersen et al. | |
| 2006/0079949 A1 | 4/2006 | Brostrom et al. | |

* cited by examiner

*Primary Examiner* — Carl H Layno
*Assistant Examiner* — Jessica Sarcione

(57) ABSTRACT

An assembly includes a medical implantable lead adapted to be attached with a distal end of the lead to an organ inside a human or animal body, the medical implantable lead being formed with an inner lumen extending along essentially the entire length of the lead. The assembly also includes a support core that has a desirable stiffness and a suitably cross sectional dimension such that it is insertable into the lumen (7) in order to increase the stiffness of the lead along its length during its working life when being implanted into a body. A method for implanting a medical implantable lead into a human or animal body makes use of such an assembly.

5 Claims, 6 Drawing Sheets

14

MEDICAL LEAD ASSEMBLY AND METHOD FOR IMPLANTATION THEREOF

BACKGROUND OF THE INVENTION

1. Field of the Invention

The invention relates to a set comprising a medical implantable lead being adapted to be attached with a distal end of the lead to an organ inside a human or animal body, wherein the medical implantable lead is formed with an inner lumen extending along essentially the entire length of the lead.

The invention also relates to a method for implanting a medical implantable lead into a human or animal body.

2. Description of the Prior Art

Medical implantable leads are used to connect a device located outside of the body or implanted just beneath the skin at a desired location, with an organ inside the body for monitoring and/or controlling of the organ. Mostly it is an electrical lead, which is adapted to receive and/or transmit electrical signals from and to the organ, respectively, such as for example an electrical lead for connecting a pacemaker or a defibrillator with a heart. However, it could also be some other kind of lead, such as e.g. a catheter for drug delivery or drainage.

The development within this field goes towards thinner leads to save space, e.g. in order to enable positioning of several cardiac monitoring and controlling leads inside the one and same vein. This also has to effect that the leads are becoming less stiff, i.e. more flexible and it is also desirable to have a highly flexible lead to affect the comfort and safety of the patient as little as possible. For example, a cardiac monitoring and controlling lead being too stiff and thin in the outermost distal end portion, could under certain circumstances penetrate into the heart wall and cause severe injuries. However, the thin leads will still have to fulfil all mechanical requirements that the leads will have to withstand during their working life and with thinner and more flexible leads, the risk for fracture of the lead will increase, since the lead may not have the sufficient fatigue resistance that is required to withstand e.g. the movements of a beating heart.

An electrical lead, is normally formed with an inner lumen, which e.g. is defined and surrounded by one or two concentric coils of one or more electrical conducting wires. The lumen is arranged to enable inserting of a guide wire during implantation of the lead, while the one or two wire coils are arranged to define the inner lumen and at the same time give the lead a sufficient stiffness. However, when the cross sectional dimension of the lead, and hence the wire coils, is decreasing, also the stiffness of the lead will decrease.

Recently, a new type of implantable electrical lead has been developed that is compatible with MRI-examination (Magnetic Resonance Imaging), i.e. a person having such an electrical lead implanted, may undergo a MRI-examination without any risk for overheating at the attachment of the distal end to the organ due to induced electric current in the lead. This is accomplished by arranging one or two electrical conductive wire coils in the lead such that sections of the coil are tightly wound, while intermediate sections are loosely wound with longer pitch and increased distance between coils of the wire. It has been discovered that a coil wound in this way will function as a LC-filter, which will suppress certain frequencies, and by carefully adapting the geometry of the lead and especially the length of the tightly and the loosely wound coil sections, respectively, it is possible to suppress or completely block the frequency of the MRI-device. However, the loosely wound sections of the lead will represent a weakened section of the lead which might lead to a subsequent fatigue fracture due to frequent movements inside the body, e.g. from a beating heart.

SUMMARY OF THE INVENTION

An object of the invention is to provide an assembly that includes a medical implantable lead, the flexibility of which can be regulated to a desired degree after implantation.

A further object of the invention is to provide a method for implanting a medical implantable lead into a human or animal body wherein the flexibility can be regulated to a desired degree after implantation.

The basis of the invention is the insight that the above object may be achieved by providing an assembly that, in addition to a medical implantable lead having an inner lumen, includes at least one support core, which is insertable into the inner lumen after implanting the lead, in order to stiffen the lead in a desirable degree. The support core can be manufactured of many different materials and designed in different ways. The assembly may include two or more support cores, having different stiffness, in order to give the physician performing the implantation, the opportunity to choose the support core which presents the best behaviour with regard to the flexing characteristics, e.g. due to a beating heart, as seen for example by X-ray imaging.

Within this general idea, the invention may be modified in numerous ways. For example, in a basic embodiment, the lead is formed with a generally uniform stiffness along its length, whereas the support core is formed as an elongated, solid fibre of e.g. a polymer having a constant cross sectional dimension and a constant stiffness along its entire length. By means of the support core, the stiffness of the lead can be increased to a desired level as soon as the lead is implanted.

However, it is also possible to manufacture a support core which is sectioned in portions having different stiffness. In this way it is possible to set different stiffness in different portions of the support core. For example, to insert a support core having a highly flexible distal portion in order to increase the stiffness in a less degree in a distal tip portion than the rest of the lead to reduce the risk of penetration into the heart wall. Another possibility is to vary the flexibility along the entire length of the lead in order to get portions having high stiffness and intermediary portions having low stiffness, wherein the portions having high stiffness are adapted to be localised at sections of a MRI-compatible lead being highly flexible and the portions having low stiffness to be localised at sections of the MRI-compatible lead being less flexible. When inserted into the lumen of an MRI-compatible lead, the lead will accordingly adopt a more uniform flexibility along its length.

The varying stiffness along the length of the support core can be achieved in different ways, e.g. by forming the support core with varying cross sectional dimension along its length, by positioning reinforcing material at the locations where the stiffness should be increased or to anneal defined portions of a support core made of a material that will get a lasting increase of the flexibility when being warmed up.

Instead of a solid support core it is also possible to form the support core as a tube having an inner lumen. Such an embodiment of the support core allows inserting of a guide wire or the like even after the support core has been inserted.

The support core can also be modified in many other ways. In order to see the lead by means of X-ray imaging and observe its motions along with e.g. the movements of a heart, it is possible to mix in or to manufacture the support core of a radiopaque material.

DESCRIPTION OF THE PREFERRED EMBODIMENTS

Figure 1:
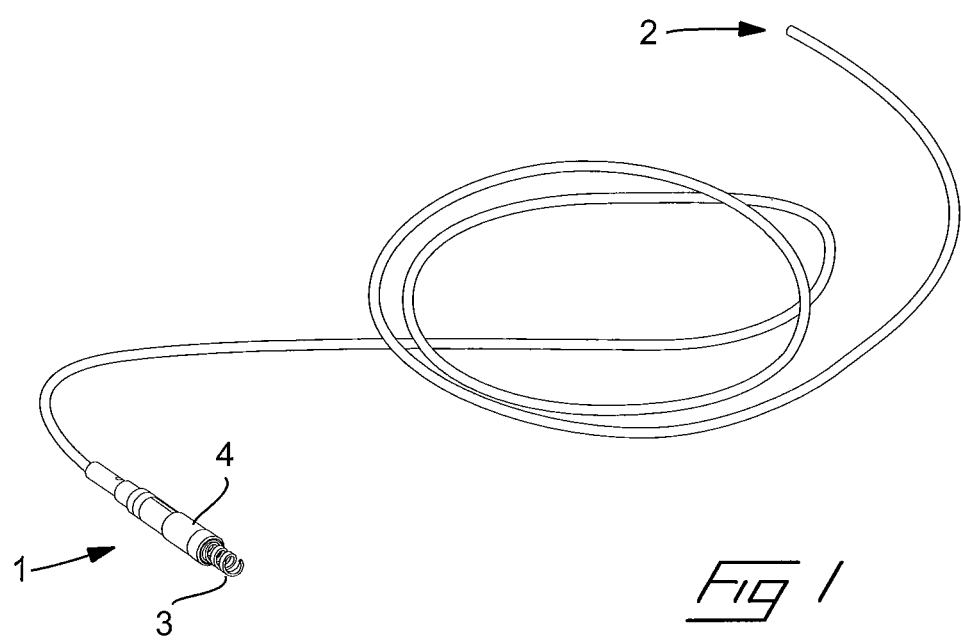
FIG. 1 is a perspective view of a known medical implantable lead.

Reference is first made to FIG. 1 in which is illustrated an example of a medical implantable lead in form of a cardiac monitoring and/or controlling electrical lead, which is adapted to be attached with a distal end 1 to heart tissue inside a heart. A proximal end 2 of the lead is adapted to be connected to a not shown pacemaker or defibrillator, which preferably is implanted immediately under the skin at a desired location. In order to accomplish the attachment of the distal end of the lead to heart tissue, the distal end is provided with a helix 3, which in a commonly known embodiment can be rotated and advanced in relation to a tube formed header 4 in the distal end, such that the helix is accommodated inside the header during insertion of the lead to the heart, whereupon the helix can be screwed out from the header and into the tissue once the distal end is positioned at a desired location. It is also possible to let the helix be fixed mounted in the distal end, wherein screwing of the helix into and attachment to the tissue is accomplished by rotating the entire lead.

An implantable lead as illustrated in FIG. 1, is flexible but it is desirable that the lead has a certain degree of stiffness. This is favourable, for example when the lead is suspended inside a chamber of the heart, in order to make the lead pliable to the movements of the heart but at the same time prevent forming of sharp bends, which in the long run may cause fatigue fracture of the lead due to the constant movements.

The desirable balance between proper stiffness and flexibility, is normally achieved by means of one or two wire coils, e.g. an inner wire coil 5 and an outer wire coil 6 as in the FIGS. 2-9. In case of two wire coils, they are coaxially arranged and the inner one can preferably be rotatable in relation to the outer and utilized to rotate and screw the helix 3 out from the header in the distal end. The inner wire coil also defines an inner lumen 7 into which a guide wire may be inserted during implantation, in order to guide the lead through narrow passages, such as veins, and to guide the distal end of the lead to a desirable location for attachment. The inner lumen can also be utilized for inserting a helix operating tool for performing rotation of the helix. When however the lead is becoming thinner, due to progressing developments, the lead might become too flexible at the same time as for example the tip portion of the lead is not allowed to be too stiff in relation to its cross sectional dimension due to the risk for penetration of the tip into heart tissue.

Figure 2:
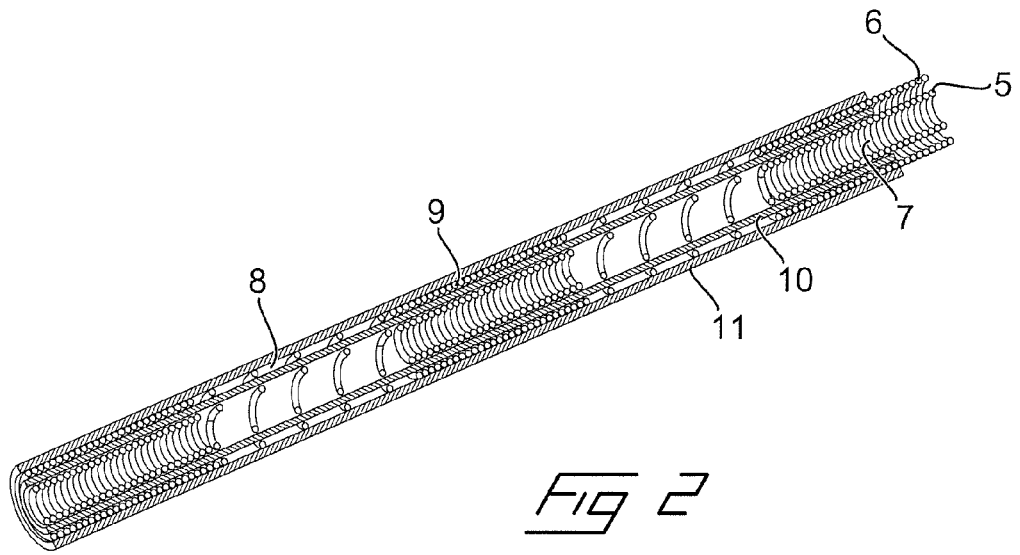
FIG. 2 is a longitudinal section through a portion of the lead according to the invention, in a first embodiment.
Figure 3:
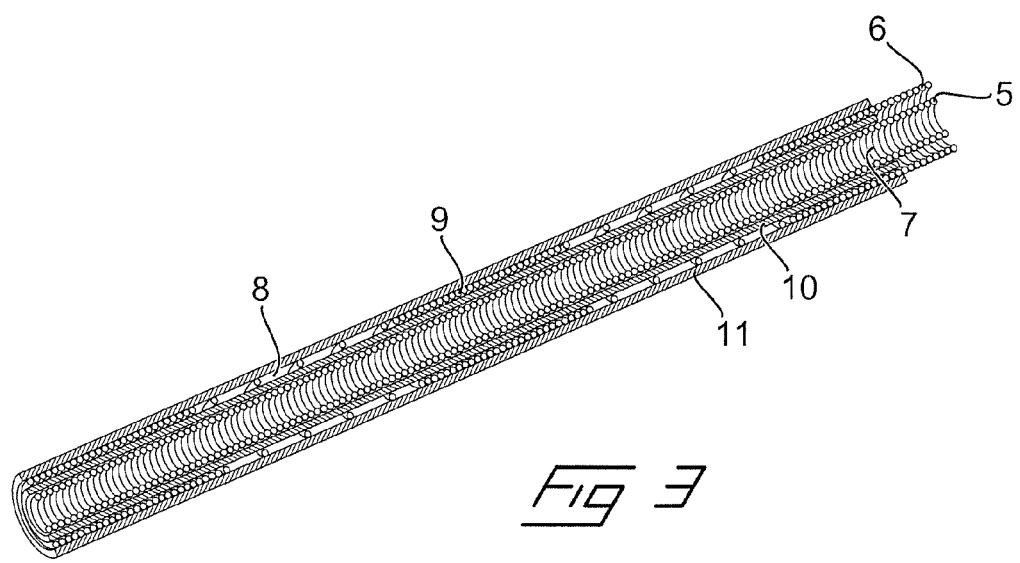
FIG. 3 is a longitudinal section through a portion of the lead according to the invention, in a second embodiment.

In FIGS. 2 and 3 are schematically illustrated two different embodiments of a new type of an implantable electrical lead, which are especially adapted for being compatible with MRI-fields. This has been achieved by arranging at least one of the outer and inner wire coils with alternating tightly wound coil sections 8 and loosely wound coil sections 9 having carefully adapted lengths and interrelation. In FIG. 2 is illustrated a first embodiment where both the inner wire coil 5 as well as the outer wire coil 6 are formed with alternating loosely wound coil sections 8 and tightly wound coil sections 9. In the embodiment in FIG. 3 on the other hand, only the outer wire coil 6 is formed with alternating loosely wound and tightly wound coil sections. The inner and outer wire coils are separated by inner and outer flexible tubes 10 and 11, respectively.

Figure 4:
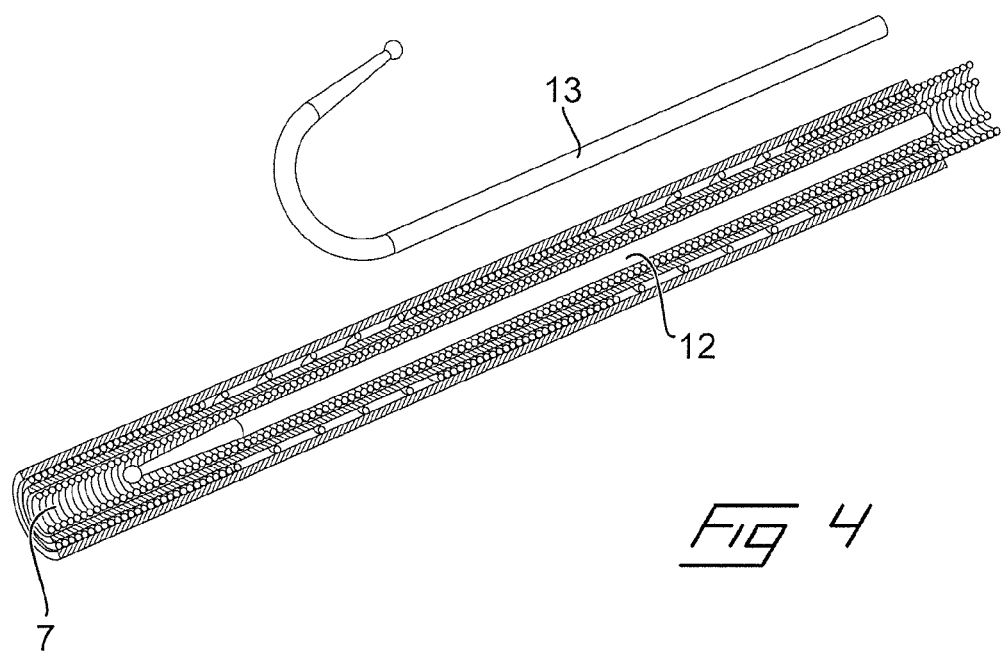
FIG. 4 is a longitudinal section through a portion of the lead according to the second embodiment of the invention, during implantation with a straight guidewire inserted in the inner lumen and a curved guidewire located at the exterior.

In both of these embodiments, the inner wire coil 5 is defining an inner lumen 7, into which a guide wire can be inserted for guiding the lead during implantation. This is illustrated in FIG. 4, where a lead according to the second embodiment, having an entirely tightly wound inner coil 5, is shown with a straight guide wire 12 inserted in the lumen. This straight guide wire can be used when passing the lead through a vein into the heart. When the distal end of the lead is positioned inside a chamber of the heart, the straight guide wire can be retracted and a curved guide wire 13 having a preformed curve in the distal end, as shown adjacent the lead, can be inserted into the lumen. By rotating the lead with the curved guide wire inside, the distal end of the lead can be pivoted such that its tip abuts against heart tissue at a desired location and then the helix is rotated and hence screwed into the tissue for attachment.

One disadvantage with an implantable lead being formed with loosely wound coil sections 8, is that the stiffness of the lead will be lowered at these sections. The stiffness of the second embodiment of the lead, according to FIG. 3, where only the outer wire coil 6 is provided with loosely wound coil sections 8, will be somewhat larger than the lead according to the first embodiment, according to FIG. 2, but the stiffness will nevertheless be lowered. Accordingly, these sections having loosely wound wire coils will deflect more due to the movements of the heart than the sections being tightly wound. The loosely wound coil sections will accordingly define zones with reduced strength, especially with regard to fatigue resistance.

Figure 5:
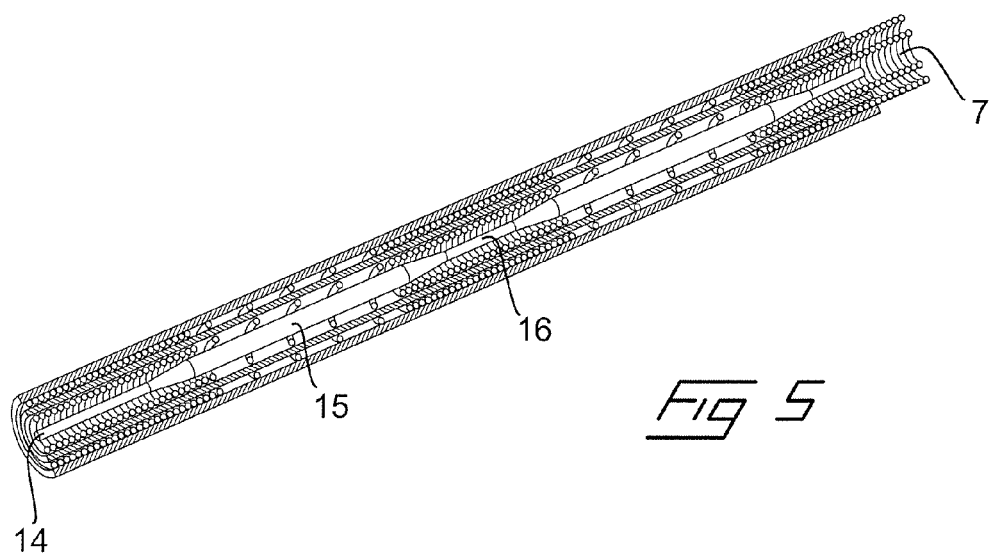
FIG. 5 is a longitudinal section through a portion of the lead according to the first embodiment of the invention, with a support core according to a first embodiment inserted into the inner lumen.
Figure 6:
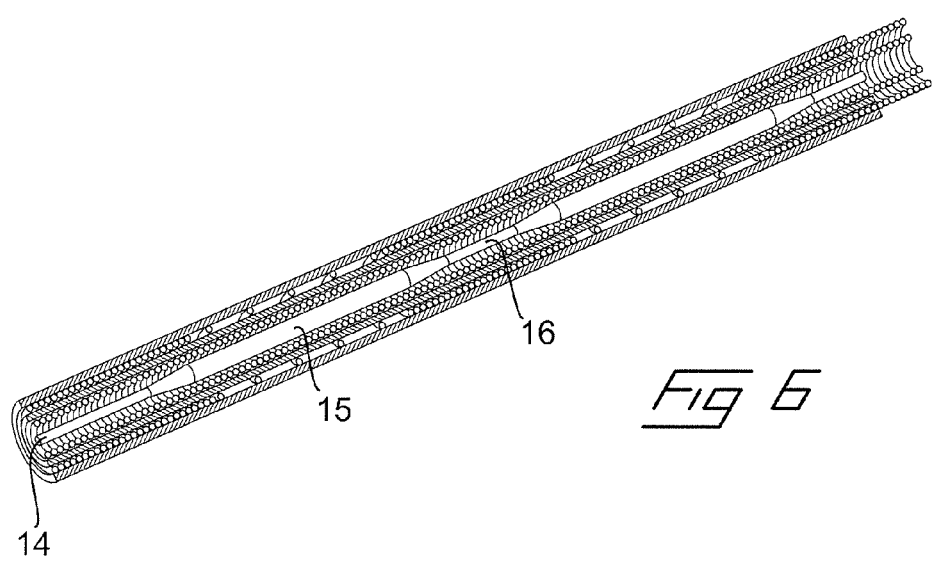
FIG. 6 is a longitudinal section through a portion of the lead according to the second embodiment of the invention, with a support core according to a first embodiment inserted into the inner lumen.

In order to overcome these disadvantages the set is, according to the invention, provided with a stiffening support core 14, which is inserted into the inner lumen 7 of the lead after implantation and which is left inside the lead preferably during the rest of its working life. In FIGS. 5 and 6 a first embodiment of a support core is illustrated inserted into a lead according to the first embodiment and the second embodiment, respectively. The support core 14 is formed with varying cross sectional dimensions along its length. More precisely, the support core is provided with portions 15 having comparatively large cross sectional dimensions, which are adapted to be localized at the sections of the lead having a loosely wound outer, and where applicable also an inner wire coil, as well as portions 16 having comparatively thin cross sectional dimensions, which are adapted to be localized at the sections of the lead which have tightly wound wire coils. By arranging a set comprising a medical implantable lead and a support core in this way, the flexibility characteristics of the lead can be equalized in a desirable degree along its length during its working life.

Figure 7:
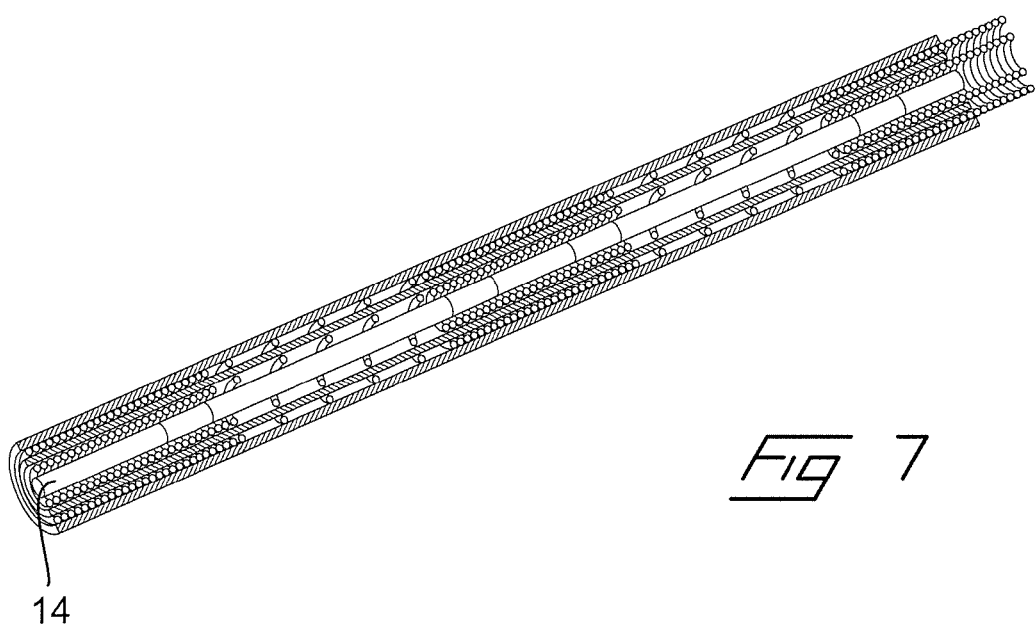
FIG. 7 is a longitudinal section through a portion of the lead according to the first embodiment of the invention, with a support core according to a second embodiment inserted into the inner lumen.

In FIG. 7 is illustrated an alternative embodiment of a support core 14 having a variable stiffness along its length. Here however, the support core is formed with a uniform cross sectional dimension along its length. Instead, the varying stiffness is achieved in some other suitable way, such as annealing a support core of a material which will maintain a reduced stiffness after being warmed up, or by arranging a reinforcing material, such as glass fibre, at the portions where it is desirable to have an increased stiffness.

Figure 8:
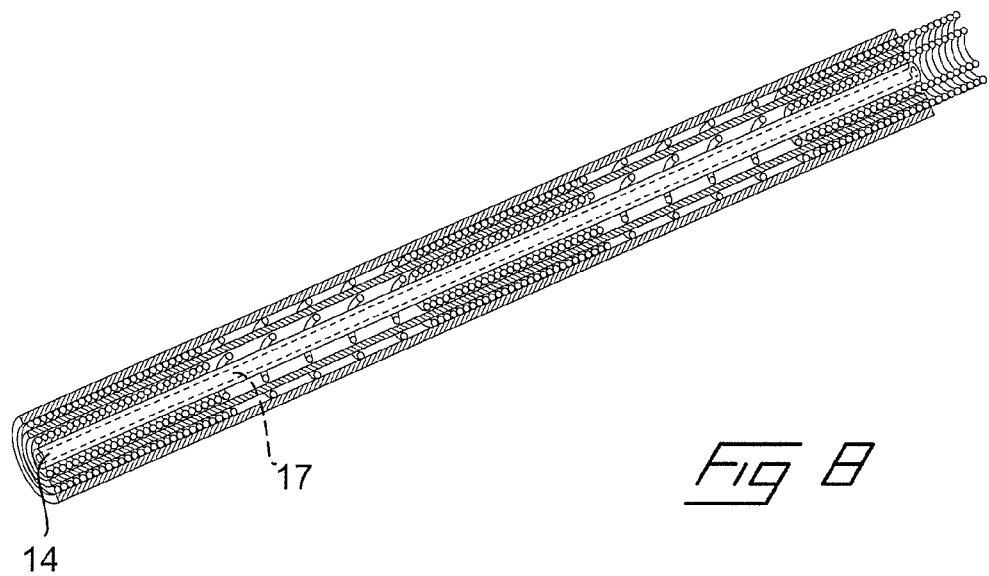
FIG. 8 is a longitudinal section through a portion of the lead according to the first embodiment of the invention, with a support core according to a third embodiment inserted into the inner lumen.
Figure 9:
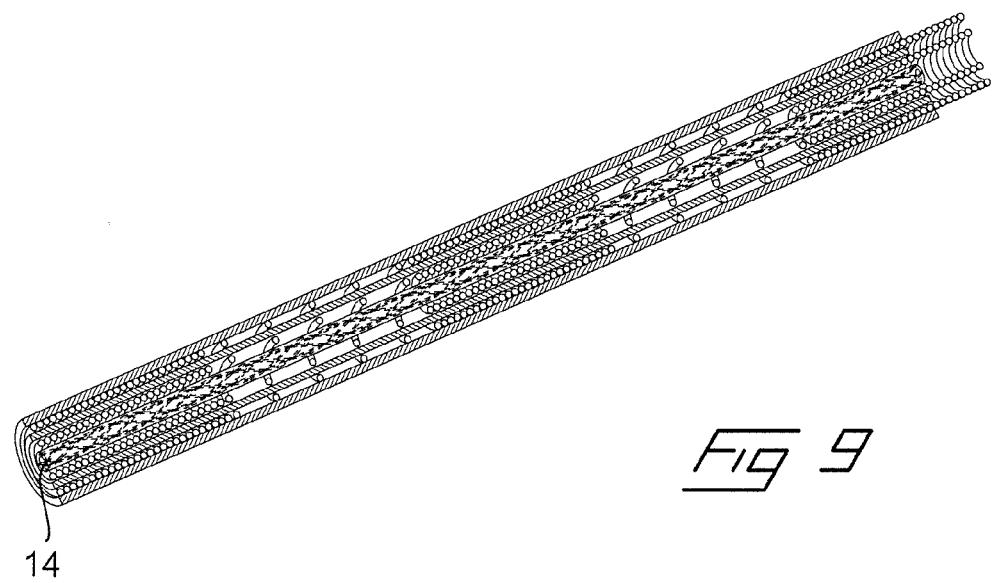
FIG. 9 is a longitudinal section through a portion of the lead according to the first embodiment of the invention, with a support core according to a fourth embodiment inserted into the inner lumen.

FIGS. 8 and 9 illustrate additional alternative embodiments of a support core 14 being in form of a thin tube having a narrow inner lumen 17. In this way it is possible to e.g. insert a guide wire or a helix operating tool to accomplish repositioning of the lead also after the support core has been inserted. The tube formed support core according to FIG. 8 is manufactured of a homogeneous material, whereas the support core according to FIG. 9 is provided with a reinforcing layer of e.g. glass fibre. In an alternative embodiment, the reinforcing layer could be applied only in portions of the support core which are adapted to be positioned at the weakened sections of the lead having a loosely wound wire coil.

Although modifications and changes may be suggested by those skilled in the art, it is the intention of the inventors to embody within the patent warranted heron all changes and modifications as reasonably and properly come within the scope of their contribution to the art.

We claim as our invention:

1. A medical lead assembly comprising:
    a medical implantable lead being adapted to be attached with a distal end of the medical implantable lead to an organ inside a human or animal body, wherein the medical implantable lead is formed with an inner lumen extending along essentially an entire length of the medical implantable lead;
    a support core having a suitable cross sectional dimension such that it is insertable into the lumen in order to increase stiffness of the medical implantable lead along its length during its working life when being implanted into a body;
    the medical implantable lead being sectioned in portions having different stiffness along its length; and
    the support core being sectioned with portions having different flexibility that inversely correspond to the sections of the medical implantable lead, and said sections of the support core being relatively located, when the support core is inserted into the medical implantable lead, to cause portions of the support core having low flexibility to be positioned at portions of the medical implantable lead having high flexibility, and vice versa;
    wherein said medical implantable lead comprises a wire coil having alternating tightly wound coil sections and loosely wound coil sections having lower stiffness as compared to the tightly wound coil sections; and
    wherein said medical implantable lead comprises an outer wire coil coaxially arranged around an inner wire coil and separated by an inner flexible tube, the outer wire coil has alternating tightly wound coil sections and loosely wound coil sections and the inner wire coil has alternating tightly wound coil sections and loosely wound coil sections, the tightly wound coil sections of the outer wire coil are aligned with the tightly wound coil sections of the inner wire coil and the loosely wound coil sections of the outer wire coil are aligned with the loosely wound coil sections of the inner wire coil.

2. An assembly as claimed in 1, wherein the support core has a high flexibility in an end portion, which is adapted to be positioned in a distal end of the medical implantable lead.

3. A medical lead assembly comprising:
    a medical implantable lead being adapted to be attached with a distal end of the medical implantable lead to an organ inside a human or animal body, wherein the medical implantable lead is formed with an inner lumen extending along essentially an entire length of the medical implantable lead;
    a support core having a suitable cross sectional dimension such that it is insertable into the lumen in order to increase stiffness of the medical implantable lead along its length during its working life when being implanted into a body;
    the medical implantable lead being sectioned in portions having different stiffness along its length; and
    the support core being sectioned with portions having different flexibility that inversely correspond to the sections of the medical implantable lead, and said sections of the support core being relatively located, when the support core is inserted into the medical implantable lead, to cause portions of the support core having low flexibility to be positioned at portions of the medical implantable lead having high flexibility, and vice versa;
    wherein the portions of the support core having low flexibility are provided with a reinforcing layer.

4. A medical lead assembly comprising:
    a medical implantable lead being adapted to be attached with a distal end of the medical implantable lead to an organ inside a human or animal body, wherein the medical implantable lead is formed with an inner lumen extending along essentially an entire length of the medical implantable lead;
    a support core having a suitable cross sectional dimension such that it is insertable into the lumen in order to increase stiffness of the medical implantable lead along its length during its working life when being implanted into a body;
    the medical implantable lead being sectioned in portions having different stiffness along its length; and
    the support core being sectioned with portions having different flexibility that inversely correspond to the sections of the medical implantable lead, and said sections of the support core being relatively located, when the support core is inserted into the medical implantable lead, to cause portions of the support core having low flexibility to be positioned at portions of the medical implantable lead having high flexibility, and vice versa;
    wherein the support core is a solid support core.

5. A medical lead assembly comprising:
    a medical implantable lead being adapted to be attached with a distal end of the medical implantable lead to an organ inside a human or animal body, wherein the medical implantable lead is formed with an inner lumen extending along essentially an entire length of the medical implantable lead;
    a support core having a suitable cross sectional dimension such that it is insertable into the lumen in order to increase stiffness of the medical implantable lead along its length during its working life when being implanted into a body;

the medical implantable lead being sectioned in portions having different stiffness along its length; and the support core being sectioned with portions having different flexibility that inversely correspond to the sections of the medical implantable lead, and said sections of the support core being relatively located, when the support core is inserted into the medical implantable lead, to cause portions of the support core having low flexibility to be positioned at portions of the medical implantable lead having high flexibility, and vice versa;

wherein the support core is a tube having an inner lumen.

* * * * *